US00PP25125P3

(12) United States Plant Patent
Sproul

(10) Patent No.: US PP25,125 P3
(45) Date of Patent: Dec. 2, 2014

(54) SHRUB ROSE PLANT NAMED 'SPROMEL'

(50) Latin Name: *Rosa hybrida*
Varietal Denomination: Spromel

(71) Applicant: CP Delaware, Inc., Wilmington, DE (US)

(72) Inventor: James A. Sproul, Bakersfield, CA (US)

(73) Assignee: CP Delaware, Inc., Wilmington, DE (US)

( * ) Notice: Subject to any disclaimer, the term of this patent is extended or adjusted under 35 U.S.C. 154(b) by 26 days.

(21) Appl. No.: 13/573,828

(22) Filed: Oct. 9, 2012

(65) Prior Publication Data

US 2014/0101796 P1 Apr. 10, 2014

(51) Int. Cl.
*A01H 5/00* (2006.01)

(52) U.S. Cl.
USPC ..... Plt./101

(58) Field of Classification Search
USPC ..... Plt./105, 106, 101
See application file for complete search history.

*Primary Examiner* — Kent L Bell
(74) *Attorney, Agent, or Firm* — Buchanan, Ingersoll & Rooney, PC

(57) ABSTRACT

A new and distinct variety of shrub rose plant is provided which forms in abundance on a substantially continuous basis attractive semi-double blossoms that are orange to apricot with red coloration toward the center of the blossoms. The vegetation is vigorous and strong and the growth habit is upright and bushy. Attractive ornamental glossy dark green foliage is formed. The plant is particularly well suited for growing in a Western landscape. Distinctive ornamentation is provided.

1 Drawing Sheet

Botanical/commercial classification: *Rosa hybrida*/Shrub Rose Plant.

Varietal denomination: cv. Spromel.

SUMMARY OF THE INVENTION

The new variety of landscape shrub rose plant of the present invention was created by artificial pollination carried out in April/May 2008 at Bakersfield, Calif., U.S.A., wherein two parents were crossed which previously had been studied in the hope that they would contribute the desired characteristics. Each parent possessed a complex parentage as indicated hereafter. More specifically, the parentage of the non-patented female parent (i.e., seed parent) can be summarized as follows: {'MORtoday'×['Geisha'×('KINbo'× 'Macivy')]}×'SPRoimpress'. The male parent (i.e., pollen parent) was the 'Sprolych' variety (U.S. Plant patent application Ser, No. 13/998,618, filed Nov. 18, 2013). The 'SPRoimpress' variety is the subject of U.S. Plant Pat. No. 21,708. The other ancestoral plants of the female parent are non-patented in the United States.

The seeds resulting from the above pollination were sown and small plants were obtained which were physically and biologically different from each other. Selective study resulted in the identification of a single plant of the new variety.

It was found that the new variety of shrub rose plant of the present invention possesses the following combination of characteristics:

(a) abundantly and substantially continuously forms attractive large semi-double blossoms that are orange to apricot with red coloration toward the center of the blossoms, (b) exhibits an upright and bushy growth habit, (c) forms vigorous and strong vegetation, (d) forms attractive ornamental dark green foliage with a glossy finish, and (e) is well suited for providing distinctive ornamentation.

A new rose variety is provided having attractive multi-colored blossoms, combined with substantially continuous blooming. The plant reblooms well and displays an attractive bushy growth habit.

The new variety well meets the needs of the horticultural industry particularly when grown in the Western landscape. It can be grown to advantage as attractive ornamentation in parks, gardens, public areas, and residential landscapes. The lavender and red blossom coloration contrasts nicely with the medium green foliage.

The new variety can be readily distinguished from its parental plants. More specifically, the female parent is a vigorous non-Hulthemia rose that displays a considerably smaller growth habit, and forms yellow-colored blossoms. The male parent displays a compact growth habit and forms ivory-cream-colored blossoms with a larger central blotch.

The new variety also can be readily distinguished from the 'Sprolem' variety (U.S. Plant Pat. No. 23,580), as well as other plants in its ancestry identified hereafter. More specifically, the 'Sprolem' variety forms bright yellow blossoms. The 'MORtoday' variety displays pink blossoms with lavender at the base. The 'Geisha' variety displays mauve blossoms. The 'KINbo' variety forms double deep yellow blossoms. The 'Macivy' variety displays very double apricot blossoms. The 'SPRoimpress' variety displays dark yellow blossoms. The 'Orangeade' variety displays orange to orange-red blossoms. The 'Auscot' variety forms very large very double yellow blossoms with dark pink at the base. The 'WEKfabpur' variety forms purple blossoms with a lighter under surface. The 'SCRivluv' variety displays single deep yellow blossoms. It is recognized that Hulthemia roses generally bloom only once a year and generally display an unattractive growth habit.

The characteristics of the new variety have been found to be homogeneous and stable and are strictly transmissible by asexual propagation by the use of cuttings from one generation to another at Wasco, Calif., U.S.A. Accordingly, the new variety can be asexually reproduced in a true-to-type manner.

The new variety has been named 'Spromel', and will be marketed under the EYCONIC and MELON LOMONADE trademarks.

BRIEF DESCRIPTION OF THE PHOTOGRAPH

The accompanying photograph shows, as nearly true as it is reasonably possible to make the same in a color illustration of this character, typical blossoms, buds, and foliage of the new variety. The illustrated plant was approximately two years of age and was growing during September, 2011 outdoors on its own roots in the field at Wasco, Calif., U.S.A.

DETAILED DESCRIPTION

The chart used in the identification of colors is that of The Royal Horticultural Society (R.H.S. Colour Chart-1995 Edition or equivalent). The description is based on the observation of two-year-old specimens of the new variety during May while growing on their own roots in a greenhouse at West Grove, Pa., U.S.A.

Class: Shrub Rose.

Plant:

*Height*.—Approximately 4 feet when mature.

*Width*.—Approximately 3 feet when mature.

*Habit*.—Upright and bushy.

Branches:

*Color*.—Young stems: near Yellow-Green Group 144B. Adult wood: near Greyed-Orange Group 165A.

*Texture*.—Young stems: smooth. Adult wood: somewhat rough.

*Thorns*.—Size: approximately 5 mm in length on average, and approximately 6 mm in width at the widest point. Quantity: numerous, and over a branch length of 13 cm approximately 35 thorns are present on average. Color on young stems: Yellow-Green Group 145B and commonly glossy. Color on mature wood: Greyed-Orange Group 177A, and blending to Greyed-Orange Group 165B on at least some tips.

Leaves:

*Size*.—A five-leaflet leaf commonly is approximately 7 cm in length on average, and approximately 5.5 cm in width on average.

*Leaflets*.—Number 3, 5, and 7. Shape: ovate with a serrate margin. Apex: pointed. Base: rounded. Texture (upper surface): smooth and glossy. Texture (under surface): smooth. Size: terminal leaflets commonly are approximately 4 cm in length on average and approximately 3 cm in width on average, and lower leaflets commonly are approximately 2 cm in length on average and approximately 1.5 cm in width on average. Color (young foliage): Yellow-Green Group 145A on the upper surface, and Yellow-Green Group 145B on the under surface. Color (fully mature foliage): commonly near Green Group 137A on the upper surface, and Green Group 137C on the under surface.

*Petiole*.—Length: commonly approximately 2.5 cm on average. Diameter: commonly approximately 1 mm on average. Color: near Yellow-Green group 144A.

*Rachis*.—Length: commonly approximately 5 cm on average. Diameter: commonly approximately 1 mm on average. Color: near Yellow-Green group 144A.

*Stipules*.—Length: approximately 11 mm on average. Width: approximately 2 mm on average. Color (upper surface): near Green Group 143C. Color (under surface): near Green Group 143A.

Inflorescence:

*Number of flowers*.—Singly or in cluster of up to approximately eight blossoms per stem, and commonly approximately 20 flowers on plant at a given time.

*Peduncle*.—Smooth in texture and commonly covered with small flexible thorns that are under 1 mm in length, near Yellow-Green Group 144A in coloration, and approximately 2.5 cm in length on average.

*Sepals*.—Number: five. Length: commonly approximately 1.8 cm on average. Width: commonly approximately 7 mm on average. Shape: lanceolate. Apex: cuspidate. Margin: commonly approximately 1 to 3 extensions having lengths of approximately 2 mm on average on three of the five sepals. Upper surface: near Yellow-Green Group 146D, and covered with short hairs. Under surface: near Yellow-Green Group 146B, and covered with short hairs.

*Buds*.—Shape: ovoid. Length: approximately 2 cm on average. Diameter: commonly approximately 1.3 cm on average. Color: Orange-Red Group 31B, and blending to Yellow-Orange Group 21C at the base.

*Flower*.—Form: semi-double, cuplike. Diameter: approximately 6.5 cm on average. Depth: approximately 3 cm on average when open. Color (when opening begins): upper surface: near Red Group 37A at the point of petal attachment, transitioning to Red-Purple Group 57A, and blending to Yellow-Orange Group 17C at the petal apex. Under surface: near Red Group 37B at the point of petal attachment, and blending to near Yellow-Orange Group 19A at the petal apex. Color (when fully open): Upper surface: near Red-Purple Group 71C at the point of attachment, transitioning to near Red-Purple Group 69C, and finally blending to near Red-Purple Group 69A at the petal apex. Under surface: near Red-Purple Group 62D at the point of attachment, and blending to Yellow Group 8C at the petal apex. Fragrance: none noticeable. Petal shape: obcordate. Petal length: commonly approximately 3.5 cm on average. Petal width: commonly approximately 3.7 cm on average. Petal margin: entire. Petal apex: broadly obcordate. Petal base: broadly cuneate. Petal texture: glabrous on both surfaces. Petal number: 8 to 12, and commonly approximately 10 on average. Petal drop: good, with the petals commonly dropping cleanly and freely. Stamen number: approximately 57 on average. Anthers: near Greyed-Orange Group 164C in coloration. Filaments: approximately 8 mm in length on average, and near Orange-Red Group 16A at the top, and transitioning to near Yellow-Orange Group 34B at the base. Pollen: commonly present in a moderate quantity, and near Yellow-Orange Group 22A in coloration. Pistils: separate and free, and commonly approximately 21 in number on average. Stigmas: near Yellow Group 11C in coloration, and approximately 1 mm in width. Styles: near Orange Group 26C in coloration and approximately 2 mm in length. Lastingness: the blossoms commonly last approximately five days on the plant under normal environmental conditions. Receptacle: circular in shape, smooth, achenes stand on the bottom and wall, approximately 7 mm in diameter, and near Yellow-Green Group 144A in coloration.

Development:

*Vegetation*.—Vigorous and strong.

*Blossoming*.—Abundant and substantially continuous.

*Resistance to diseases*.—Typical for the type with the plant being best suited for growing in the Western States.

*Propensity to form hips/seeds*.—Sparse.

*Hardiness*.—U.S.D.A. Hardiness Zone Nos. 6 to 9.

Plants of the new 'Spromel' variety have not been observed under all possible environmental conditions to date. Accordingly, it is possible that the phenotypic expression may vary somewhat with changes in light intensity and duration, cultural practices, and other environmental conditions.

I claim:

1. A new and distinct variety of shrub rose plant characterized by the following combination of characteristics:

(a) abundantly and substantially continuously forms attractive large semi-double blossoms that are orange to apricot with red coloration toward the center of the blossoms, (b) exhibits an upright and bushy growth habit, (c) forms vigorous and strong vegetation, (d) forms attractive ornamental dark green foliage with a glossy finish, and (e) is well suited for providing distinctive ornamentation; substantially as herein shown and described.

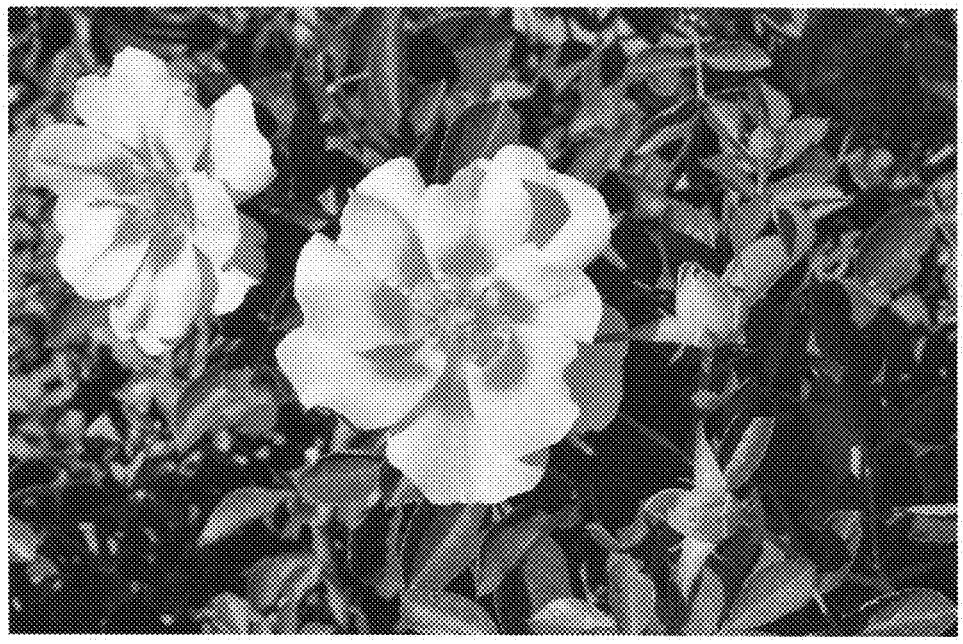

* * * * *